United States Patent [19]

Curlee

[11] Patent Number: 4,682,587
[45] Date of Patent: * Jul. 28, 1987

[54] COMPOUND FORCE SACRO-LUMBAR SUPPORT BELT

[75] Inventor: James D. Curlee, Mechanicsburg, Pa.

[73] Assignee: Pneumedic Corp., Palmerton, Pa.

[ * ] Notice: The portion of the term of this patent subsequent to Nov. 18, 2003 has been disclaimed.

[21] Appl. No.: 731,392

[22] Filed: May 7, 1985

[51] Int. Cl.[4] ............................ A61F 5/01; A61F 5/04
[52] U.S. Cl. ............................... 128/78; 128/DIG. 20
[58] Field of Search ............... 128/78, DIG. 20, 89 R, 128/69, 75, 82, 84 R

[56] References Cited

U.S. PATENT DOCUMENTS

| | | | |
|---|---|---|---|
| 1,646,590 | 10/1927 | Mildenberg | 128/DIG. 20 |
| 3,521,623 | 7/1970 | Nichols et al. | 128/78 |
| 4,135,503 | 1/1979 | Romano | 128/78 |
| 4,178,922 | 12/1979 | Curlee | 128/78 |
| 4,178,923 | 12/1979 | Curlee | 128/DIG. 20 |
| 4,552,135 | 11/1985 | Racz et al. | 128/78 |

FOREIGN PATENT DOCUMENTS

| | | | |
|---|---|---|---|
| 1461408 | 6/1965 | France | 128/78 |
| 163116 | 3/1980 | Netherlands | 128/78 |
| 117148 | 7/1918 | United Kingdom | 128/78 |
| 985591 | 3/1965 | United Kingdom | 128/DIG. 20 |

Primary Examiner—Edgar S. Burr
Assistant Examiner—Tonya Lamb
Attorney, Agent, or Firm—Sanford J. Piltch

[57] ABSTRACT

Disclosed is an improved therapeutic support belt adapted for the sacro-lumbar region of the human body, having a flat envelope of more or less rectangular configuration that is capable of receiving and storing fluid. The envelope is provided with a plurality of vertical ribs perpendicular to the longitudinal axis of the envelope, the ribs forming a series of intercommunicating inflatable cells. The envelope is capable of attachment to a belting or corseting material with fastening straps, and has a means of introducing fluid therein.

1 Claim, 7 Drawing Figures

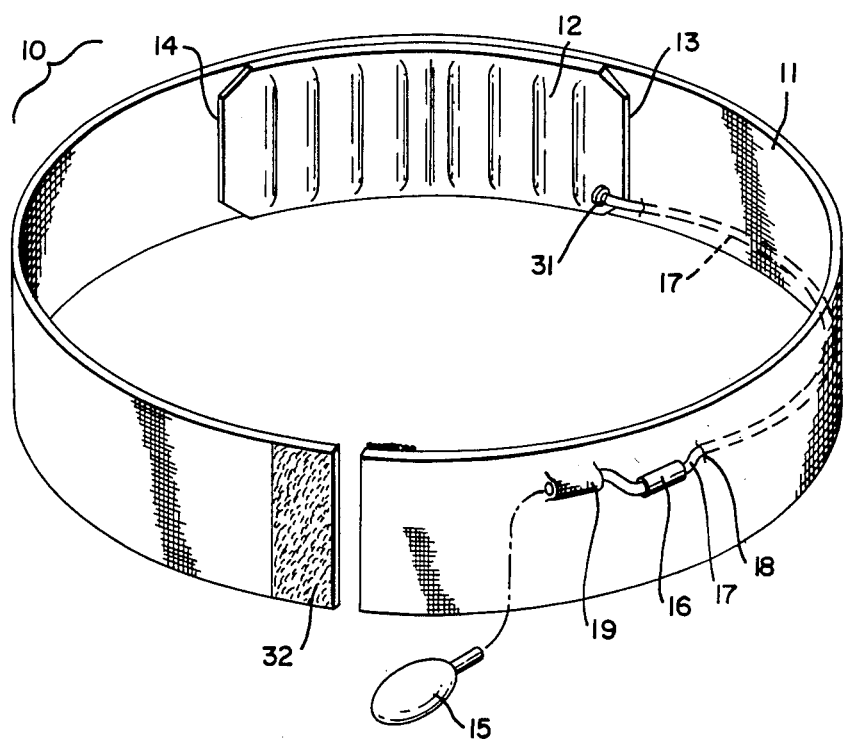
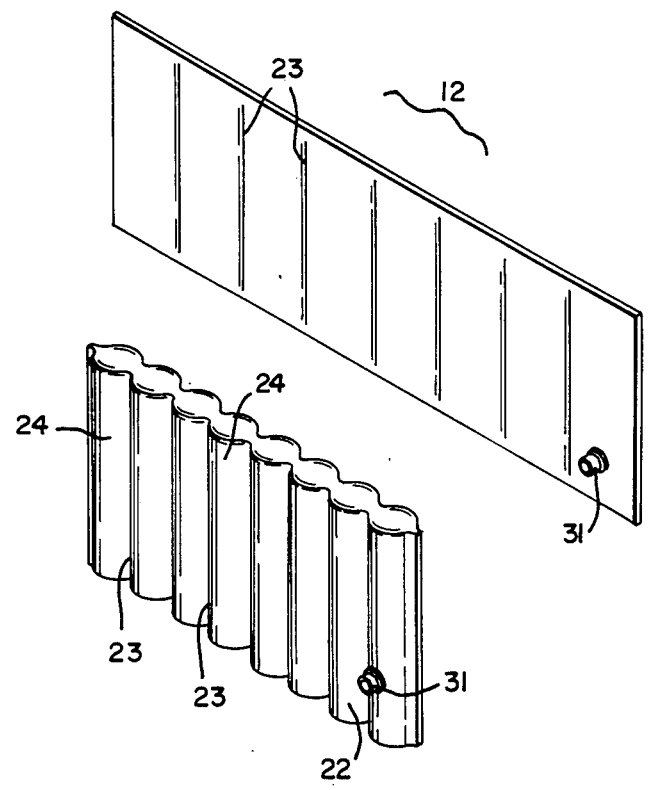

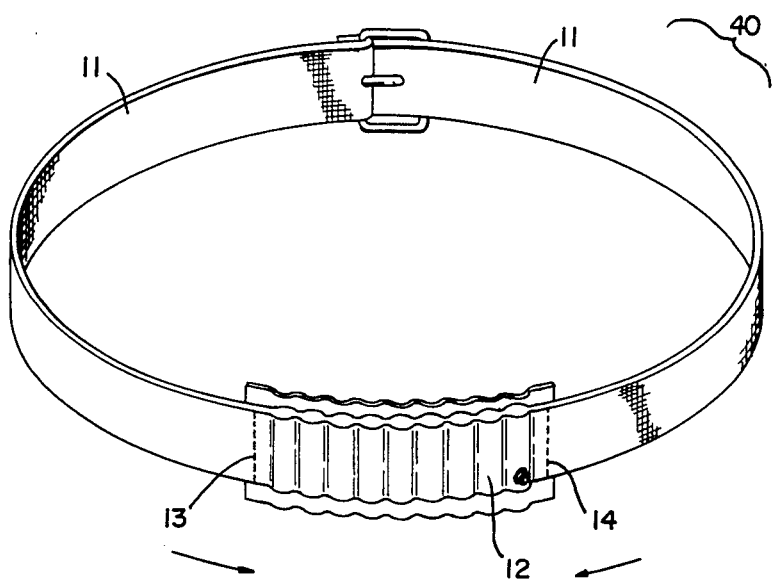
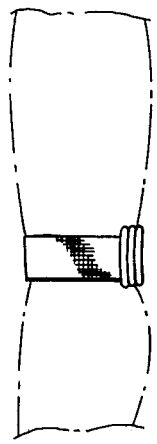
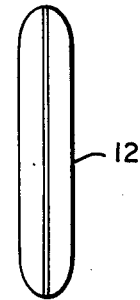
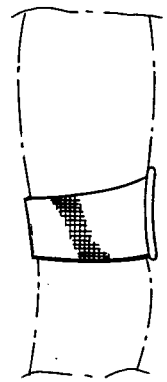
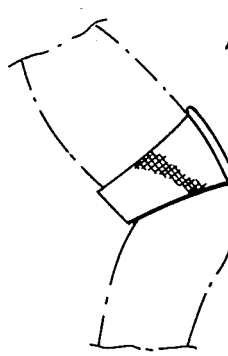

COMPOUND FORCE SACRO-LUMBAR SUPPORT BELT

FIELD OF THE INVENTION

The compound force support belt of the present invention relates generally to therapeutic support devices and, more particularly, to a belting appliance for providing pressurized support to the sacro-lumbar region of the human back for the prevention and/or treatment of injuries to the aforesaid region.

BACKGROUND OF THE INVENTION

As is well known, back injuries comprising minor displacement or misalignment of one or more vertebrae can cause pressure to be exerted upon spinal nerve roots. This pressure commonly results in severe pain and consequent restriction of movement for the victim. It is also commonly known that if the particular misaligned vertebra is realigned in conjunction with the residual, properly aligned vertebrae, the pressure on the spinal nerve is alleviated and thus the pain suffered by the victim is relieved.

This realignment of misaligned vertebrae is normally accomplished as a result of pressure being applied to the afflicted area of the body. In accordance with these principles, prior art therapeutic appliances have been developed in order to provide such counter-pressure to the afflicted area as required.

MATERIAL INFORMATION DISCLOSURE

Many of these prior art appliances utilize an inflatable bladder means that seeks to exert counterpressure at a precise body location as a result of the inflated expansion thereof. U.S. Pat. No. 4,135,503, to Romano, for example, teaches the use of an inflatable bladder affixed between a rigid base plate and an apperturned template plate. U.S. Pat. No. 4,178,922, to Curlee, teaches an inflatable bladder means inserted within a one-piece synthetic plastic body encircling member. Most recently, prior development of the present inventor, U.S. Ser. No. 591,501, Curlee, and U.S. Ser. No. 627,462, Curlee, have taught the use of inflatable bladders in conjunction with a support surface.

Support appliances, such as those cited above, which utilized rigid metal or plastic ribs or backing, have the disadvantage of failing to provide support for the human back throughout a wide range of motion, because once such support surfaces are bent or set in a particular curve, they will not yield. Indeed, such rigid stays, ribs, support backing, etc., found in these therapeutic devices are there to prevent most movement. This results not only in extreme discomfort to the wearer, but such lack of movement has been known to weaken muscles after the prolonged use of such devices. The device of the present invention overcomes these and other disadvantages by providing a compound force sacro-lumbar support that provides both abdominal and sacro-lumbar support to the wearer and allows supported movement throughout a wide range of motion.

Previous inventions dealing with back support by J.D. Curlee have centered around the use of inflatable cells which press upon the back in a predetermined manner and position. This is opposed to having a bladder inflate with air against the back and cover a broad area without control or predictability. This predictability of contact and positioning was achieved by means of sectioning off a bladder into several communicating parts and also by attaching rigid or semi-rigid material to the bladder to control its shape and movement under the pressure of inflation.

After much experimentation with bladder sections and shapes plus various methods of attachment to a belt or corseting material, a surprising and very desirable effect upon the body was found to occur during inflation of the bladder.

The two-way force effect is brought about by (1) inflation of the specially designed bladder forming a rigid yet flexible support structure across the back and (2) simultaneous tightening of the belt or corset material (strapped or buckled in a conventional manner in front or side) which occurs from the rear.

This highly desirable compound simultaneous force acting on the wearer's body pushes against the back and pulls the abdominal wall toward the spine. The waist is not so much squeezed or pinched in as usually happens when the two ends of a belt are brought together. Rather, drawing the belt tighter from a point on either side of the spine at the rear of the back reduces pinching force and enhances purely structural support in front.

The design elements which make the compound force possible are defined as follows. A flat envelope is sectioned into a series of vertical ribs along a more or less rectangular plane, the length of the entire envelope being much longer than its height, which make up a series of multiple pressure cells which inflate to a series of vertical tubular ribs.

The ends of the envelope are sewn or suitably attached to a belting or corseting material. When the belt or corset material is affixed in front by belt buckles, snaps, hooks or other suitable means, and the envelope is inflated, the compound force takes place. The ribs inflate and the overall length of the envelope shrinks. This draws the belt or corset tighter around the waist, pulling the abdomen inward toward the spine.

The envelope always shrinks along a line perpendicular to the tubular length of the inflating ribs. The amount of air pressure inside the envelope determines the amount of shrinkage. The degree of shrinkage along the length of the envelope is also determined by the shape and volume of each ribbed segment. For instance, an envelope measuring 18 inches wide by 6 inches high will inflate to a tubular shape with minimal shrink along its longest length. It will also diminish somewhat in height. In order to achieve significant shrink, it is necessary to seam or section the envelope into numerous divisions, each perpendicular to the direction of shrinkage (from end to end of the 18 inches). Thus, an envelope with seams one inch apart, with a small air passage from section to section will inflate 18 individual tubes. This has the effect of maintaining roughly the 6" height but causing significant shrinkage from end to end of several inches along its longest measurement. Shrinkage in one direction only is extremely valuable in the application for back support. The ribs maintain their roughly 6 inches of height, top to bottom and thereby offer support to the back parallel to the spine. Another desirable effect of the shrinkage is to make each inflated tubular shaped rib bow inward in a concave manner to conform to the concave shape of the human anatomy. The constant tension of the shrink effect insures that the tubular ribs will always conform to the anatomy during a full range of movement such as bending forward, which rapidly changes the back's anatomy from concave to convex. As the array of verticular tubes wrap around the wearer's back, the stabilizing effect of their individual resiliency will not be lost. Support appliances with rigid metal or plastic ribs do not provide support for the back throughout a wide range of motion, because once bent or set in a particular curve, they will not yield. But a back support which both supports and allows supportive movement throughout a wide range of motion is far more therapeutic. Rigid stays, ribs, plastic shapes, etc., found in common back support devices are there to prevent most movement. It is not only extremely uncomfortable to the patient but lack of movement has been found to weaken muscles with prolonged wear. The rigidity of each inflated vertical tube is quite substantial on its own and has been found to provide adequate support without the aid of metal or plastic stiffeners. By eliminating fixed rigid support elements there is greater comfort and mobility.

Not only is the air pressure within each tubular rib responsible for its ability to act as a support structure, somewhat parallel to the spine, but the actual contact of each tube serves to act on the spindle mechanism of muscle tissue and thereby force spasmed muscles to relax. Tight, unyielding muscles which have contracted involuntarily present a particular danger—tender muscle tissue is apt to rip and tear as the person bends or reaches. A ballistic stretch occurs. Such constant trauma to the muscular support system of the back weakens entire muscle groups and throws extra strain on support ligaments which have very little resiliency on their own. Therefore, it is important that back muscles remain flexible and able to naturally elongate as body movement dictates. Multiple pressure points provided by the numerous inflated ribs help maintain flexibility by virtue of the substantial pressure each inflated section provides. This is not possible with ordinary back supports.

Variation of Shapes. The actual sectioning of the envelope, whether shaped as a rectangle, oval, square, or other multi-sided design can take on variations of the ribs themselves. The direction of the ribs do not have to be precisely perpendicular to the direction of shrinkage. Nor must the tubes be perfectly straight. They may curve in a variety of direction with a mixture of designs within one envelope. The exact number of tubes within the envelope may vary along with individual size. There may be areas of the envelope which do not inflate. The tubes or ribs may be made in any suitable manner, not necessarily limited to two flat pieces of material which is then sealed into the appropriate sections. A preferred shape is rectangular.

Belting. The inflatable envelope with its various chambers can be attached to practically anything which binds around the individual. This can be a simple belt, corset, garment, wrap, sash, surgical dressing or tape. The free ends of the envelope can be sewn, stapled, rivited, or attached in any suitable fashion. The envelope can even be glued over its entire area within a belt or wrap. The finished assembly of envelope and belt or wrap may be all that is needed to do the job or this assembly can be converted over or completely hidden within a suitable material, padded or unpadded.

Air Access. A major consideration is the placement of a valve(s) or air pump which makes it easy and practical for the wearer to inflate.

To make the belt ergonomically practical in terms of its function for sports, work, and relaxation, a preferred place was found at which point a pump/relief valve could be permanently affixed. This is located at an angle a few degrees either side of where the person's arms naturally hang. If it is more than a few inches toward the rear, the pump and valve will be difficult to reach. If the pump/valve mechanism is too far forward, it will interfere with lifting of objects. The position described does not interfere with sitting or lifting of objects. A tube protrudes from the bladder, through the belting material and/or covering, if any, to which a pump/valve assembly is attached. The position can be either right hand or left hand.

For the belt or corset which has only a check valve connection for hook up to a squeeze pump, the best location has been found to be a few inches to the left or right of the front center of the body. This position of the check valve allows easy insertion of the pump and best position of the hand for inflation. The ideal position for the check valve is near the top edge of the belt or corset where it can be easily seen by the wearer.

A tube leads from the air envelope forward around the side and protrubes through the belting or covering material. A check valve is affixed where it can be held in one hand and a squeeze pump can be inserted for inflation by the other hand. When the pump nozzle is taken away, the air remains inside the envelope. A pocket can be provided in which the valve may be kept from dangling loosely.

If the check valve is placed more than 5 or 6 inches to the rear of center, in front of the wearer (depending on the size of the wearer's waits), insertion of the pump nozzle and actual squeezing of the bulb becomes more difficult. The valve may be placed either right or left of front center.

Another important placement of the valve is directly in the center of the back or a few inches to either side. This allows the belt or corset to be inflated by another person, such as a nurse in an operation room. Doctors and nurses wear operating gowns which tie together up the back. Placement at the back allows another person to slip the nozzle into the valve through the opening of the gown.

When the belt or corset is worn inside regular clothing, placement of a valve at the front as described above allows a person to reach the valve through the opening in a blouse or shirt, usually by undoing no more than one button. Thus, the wearer need not disrobe simply to change the tightness of the belt or corset.

Summary of the Invention

This invention is a compound force sacro-lumbar support belt with an inflatable envelope which has been sectioned off in such a manner as to make it shrink significantly along a single axis while maintaining the dimension more or less along another axis usually perpendicular to the first.

The envelope, when attached to a belting or corset material at the two contracting ends, will "pull" the belting or corset tighter about the wearer's waist from points at either side of the center of the rear. The effect is to increase abdominal pressure while at the same time apply predetermined pressure points at the back. An increase of abdominal pressure is desirable during lifting as it decreases pressure within the lumbar discs. Concentrated pressure points from the sectioned envelope, as they expand under air pressure, are desirable for the effect they have on releasing the tension within spasmed back muscles. The pressure points work on the muscle's spindle mechanism to signal a return to a normal, relaxed, or elongated state. Preventing spasms in the back not only reduces the pain of backache, but it prevents the chance of ripping and tearing of muscle tissue due to a ballistic stretch or overextension of muscle tissue. The compound action of expanding air cells and simultaneous tightening of the belt or corset assures constant contact during a full range of bodily motion between the back and the expanding tubular air cells. When the back is straight, it has a natural concave shape which the vertical tubes assume. When a person bends over, the back assumes a convex shape which the inflated tubular ribs conform with. Thus, the wearer has a stabilizing support regardless of movement. This is in stark contrast to other back supports which tend to restrict movement. They have preformed metal ribs or plastic inserts which lose their ability to properly contact the back during a full range of movement or they do not allow the movement at all. Some support devices actually become loose during certain movements and all contact with the back can be lost at the critical areas. However, the shrink effect assures that the belt or corset will always be in tension regardless of bending or stretching and thereby keep the important points of contact for stability and support.

The flexible yet sufficiently rigid inflated vertical ribs eliminate the need for stiffeners such as metal or plastic which cannot adapt to the changing contours of the body during motion.

Planned, ergonomic placement of the air pump and/or check valve makes air inflation and function of the belt or corset easy and convenient. One need not disrobe to increase or release tension as required with most other supports when worn under regular clothing.

The foregoing and other objectives of the present invention are achieved by providing an inflatable envelope that is sectioned into a series of vertical ribs along a more or less rectangular plane, the length of the entire envelope being much longer than its height (3-5 times). Said ribs result in the formation of a plurality of intercommunicating pressure cells which inflate to a series of tubular supports. The ends of the envelope are sewn or suitably attached to a belting material. Said belting material is provided with a means of attaching itself around the waist of the wearer. A means of introducing fluid into said envelope is provided, whereupon said ribs inflate, resulting in a shrinkage of the overall length of the envelope. Said shrinkage draws the belt tighter around the waist of the wearer, thereby providing concurrent support to the sacro-lumbar area as well as to the abdominal area.

DESCRIPTION OF THE FIGURES

Various additional objects, features, and advantages of the invention will be better understood from the following description when considered in conjunction with the accompanying figures, to-wit:

FIG. 1 is a perspective view of the compound force sacro-lumbar support belt.

FIG. 2 is a perspective view of the inflatable envelope both before and after the introduction of fluid.

FIG. 3 is a perspective view of the compound force sacro-lumbar support belt after inflation.

FIG. 4 (a-d) shows an expanded bladder with tubular ribs expanded against the back to form a rigid yet pliable support for the back to form a compound support action.

SPECIFICATIONS OF THE INVENTION

As can be seen in FIG. 1, the compound force sacro-lumbar support belt, generally designated as 10, is comprised of a flexible belting material 11 which is capable of wrapping around the waist of the wearer. An envelope 12 may be disposed either upon or within the belting material 11 at a point that would insure contact with the wearer. In the present preferred embodiment, said envelope 12 is of substantially rectangular configuration, its length being approximately 3 times its width. The envelope 12 is secured to the belting material 11 at points 13 and 14, along the extreme ends of the envelope by stitching, adhesives, or other suitable means. The envelope may also be glued over its entire area to the belting material. In alternative embodiments, the envelope may be disposed within a multi-ply belting material, or may also be constructed so that the envelope material itself, which must possess a low coefficient of stretchability, extends beyond the area of inflation, to form the belting material. The envelope portion is defined by stitching, adhesives or other suitable means capable of forming a bladder for the reception and retention of fluid.

The support 10 is further provided with an air pump 15 used in conjunction with a check valve 16, said valve 16 being adapted to readily receive said pump 15 for the introduction and retention of fluid within the envelope 12. In the present embodiment a flexible tube means 17 is provided, said tube connecting an entry port 31 in the envelope 12 with the check valve 16, running through the belting material 11 around the side of the wearer. An opening 18 is provided in the belting material 11 through which the tube 17 protrudes and the check valve 16 is attached. The belting material 11 is further provided with a tubular protrusion 19 which may be constructed of a unitary material with said belt 11. Said protrusion 19 is of dimensions suitable for removably engaging and securing the air pump 15. In its preferred embodiment, the location of the opening 18 and the tubular protrusion 19 is not more than 6 inches on either side of the front center of the wearer. The belting material 11 may be secured by VELCRO strips 32 or any suitable securing means.

FIG. 2 shows the envelope portion 12 of the compound force sacro-lumbar support in both its uninflated 21 and inflated 22 state. The envelope 12 can be constructed of any suitable material that is air tight and possessing a low coefficient of stretch-ability. As can be readily seen, the envelope 12 is provided with a series of ribs 23 more or less parallel to each other, being more or less perpendicular to the longitudinal axis of the envelope. Said ribs need not be precisely perpendicular to said axis but may be adjusted slightly to accommodate variations in design, such as mild curves in essentially perpendicular alignment. Said ribs 23 may be formed by any suitable means, such as stitching, adhesives, or other types of sealing. The envelope 12 is further provided with an entry port 31 for the introduction of fluid therein.

Upon inflation 22 it can be seen that the ribs 23 form a series of intercommunicating inflated cells 24, which, again, are of a nesting, essentially parallel configuration, essentially perpendicular to the longitudinal axis of the envelope 12. Upon inflation 22 the envelope 12 will shrink along a line perpendicular to the tubular length of the inflated cells 24, the amount of air pressure inside the envelope 12 determining the amount of shrinkage.

The degree of shrinkage along the length of the envelope 12 is also determined by the shape and volume of each ribbed cell. An additional effect of the shrinkage is to make each inflated cell bow inward in a concave manner to conform to the concave shape of the human back.

The advantages of the shrinking effect can be best understood by turning to FIG. 3, wherein the compound force sacro-lumbar support can be seen as inflated 40. The envelope 12, when attached to the belting material 11 at the two contracting ends 13 and 14, will pull the belting material 11 tighter about the wearer's waist from points 13 and 14 at either side of the center of the rear of the belt 11. The effect is to increase abdominal pressure while at the same time applying predetermined pressure points at the back. It should be noted that an increase of abdominal pressure is desirable during lifting by the wearer, as it decreases pressure between the lumbar discs. Pressure points from the inflated envelope as it expands under air pressure is desirable for the effect it has on releasing tension within spasmed back muscles, said pressure points affecting the muscle's spindle mechanism to signal a return to a relaxed, elongated state. This compound action of expanding air cells and simultaneous tightening of the belting material 11 results in constant contact with afflicted areas during a full range of bodily motion by conforming to the variations in shape of the back during activity.

The compound support action can be seen in FIG. 4a wherein the belt is shown wrapped snuggly around the waist of a human body. Air is introduced into the bladder and the compound, simultaneous action takes place. Shrinkage from points at the rear of the belt pulls on the stomach/abdomen for extra support. Tubular ribs expand against the back to form a rigid yet pliable support for the back. FIG. 4b shows a side view of the tubular support rib; bladder material expands under pressure and each sectioned area forms a rigid rib which presses against the back. The amount of rigidity and support is controlled to an infinite degree by the amount of air pressure introduced. These tubular ribs conform to the concave shape of the back (FIG. 4c) when made part of a belt or corset. Under pressurization, they constitute an effective support for the sacro-lumbar area. When a person bends forward, the curvature becomes convex and the tubular ribs conform automatically when part of a belt or corset. The shrink effect keeps the belt in constant tension and thus keeps the ribs against the back.

What is new and desired to be secured by letters patent is:

1. A compound force sacro-lumbar support belt comprising an inflatable envelope, said envelope being divided into a multitude of intercommunicating, parallel ribs disposed perpendicular to the longitudinal axis of said belt, means to introduce fluid to said envelope and to retain said fluid within said envelope, upon introduction of fluid said envelope shrinking along its length and said ribs contacting the wearer and providing lines of pressure in the sacro-lumbar region, said envelope being constructed of a material having relatively no stretchability compared to the amount of shrinkage, said shrinkage and said ribs being the only means of support to the sacro-lumbar region, means to secure said envelope to said wearer, said means to secure being two flexible straps.

* * * * *